United States Patent [19]

Gundlach

[11] 4,369,652
[45] Jan. 25, 1983

[54] METHOD FOR MEASURING THE VOLUME OF SOLID BODIES AND A MEASURING AND/OR REFERENCE CHAMBER FOR PERFORMING SAID METHOD

[75] Inventor: Bertus L. Gundlach, Wageningen, Netherlands

[73] Assignee: De Rijkslandbouwhogeschool, Wageningen, Netherlands

[21] Appl. No.: 233,591

[22] PCT Filed: Jun. 5, 1980

[86] PCT No.: PCT/NL80/00020
§ 371 Date: Feb. 3, 1981
§ 102(e) Date: Feb. 3, 1981

[87] PCT Pub. No.: WO80/02639
PCT Pub. Date: Dec. 11, 1980

[30] Foreign Application Priority Data

Jun. 5, 1979 [NL] Netherlands ............... 7904400

[51] Int. Cl.³ .................................... G01F 17/00
[52] U.S. Cl. ............................................. 73/149
[58] Field of Search ................................. 73/149

[56] References Cited

U.S. PATENT DOCUMENTS 3,769,834 11/1973 Fletcher .
4,083,228 4/1978 Turner .
4,112,738 9/1978 Turner .
4,184,371 1/1980 Brachet .

FOREIGN PATENT DOCUMENTS 2256923 6/1974 Fed. Rep. of Germany .
2412825 7/1979 France .
1543708 4/1979 United Kingdom .

OTHER PUBLICATIONS

Modern Plastics., 37 (1960.06), 10, 50, article entitled "New Machinery".
Machine Design, vol. 49, No. 2, (1977 01), p. 46.
Machine Design, 32 (1960, 03, 17), 6, 12.

Primary Examiner—S. Clement Swisher
Attorney, Agent, or Firm—Fleit & Jacobson

[57] ABSTRACT

Determination of the volume of solid bodies by plethysmometry: the bodies, such as human beings or animals, are brought into a measuring chamber (1) the volume of which is changed by means of a piston (8) within a cylinder (7). The change in pressure within the chamber (1) is measured and constitutes a measure of the volume of the body to be determined. The measurement may be performed with the aid of a reference chamber (5) in which the volume is also changed, i.e. by simultaneous movement of a piston (11) within a cylinder (10) together with piston (8) within cylinder (7). By comparison of pressures (by means of 17) between the chambers (1 and 5) a more accurate volume measurement is obtained than without reference chamber (5). The invention is based on the recognition that a quick change in volume is conducive also to a change in temperature and that living beings to be measured give off water vapor and heat, thus causing the measurement to be less accurate, and that this problem may be solved by filling the measuring chamber (1) and preferably also the reference chamber (5) for the major part thereof with a solid filler material (2, 6) having a plurality of interconnected cavities.

9 Claims, 1 Drawing Figure

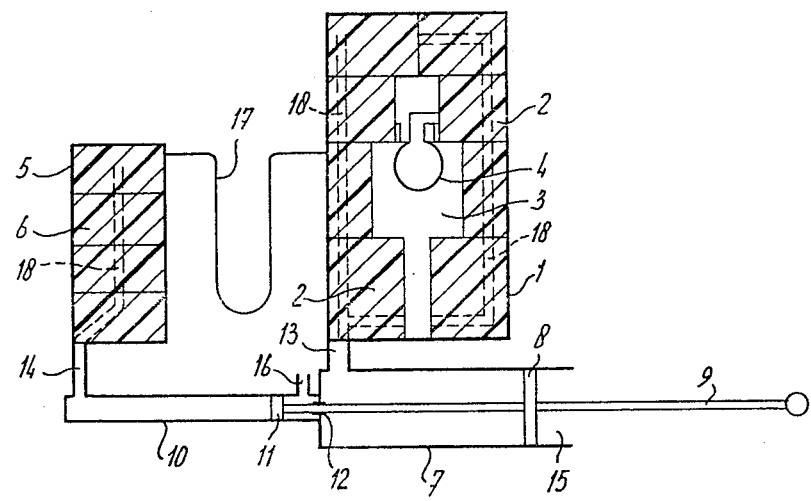

METHOD FOR MEASURING THE VOLUME OF SOLID BODIES AND A MEASURING AND/OR REFERENCE CHAMBER FOR PERFORMING SAID METHOD

The invention relates to a method for measuring the volume of solid bodies and to a measuring and/or reference chamber for performing said method.

It is often desired to determine the volume of human beings and animals e.g. for medical control purposes, for determining metabolic effects of food, for determining the merchandise value of animals, etc. in which often the weight should also be determined in order to calculate the specific density on the basis of both said data.

In a known method for determining the volume of bodies there is performed a weighing both in air and under water. With respect to the weighing under water, this method is difficult to perform or even completely objectionable in case of e.g. old people, children, patients and many animals.

Accordingly it has been attempted to provide a measurement of the volume of solid bodies that may be carried out more easily by performing the measurement by plethysmometry, i.e. by inserting the body to be measured in a chamber in which the body to be measured is accomodated excluding the chamber from the surroundings, changing the volume of said chamber to a predetermined known extent and measuring the change in pressure caused by said change in volume.

The advantages thereof are that the measurement may be performed by means of a simple apparatus and that in case of human beings and animals the volume of the lungs and other corporal cavities filled with gas are not included in the measurement in as far these cavities are in a more or less free pressure equalizing connection with the exterior of the body. Furthermore the method may well be applied for old people, patients, children and all kinds of animals without any objection.

In plethysmometry there is however the drawback that a relatively quick change in volume not only induces a change in pressure but causes also a change in temperature to an extent not known accurately whereas in case of human beings and animals the object to be measured gives off water vapour and heat causing the measurement to be even less accurate. In order to avoid this drawback as much as is possible one may perform the compression very slowly, while also in case of a quickly performed compression there may be a restoration of the initial temperature so that the pressure will then yield a more proper picture of the volume in view of the isothermal compression thus simulated indirectly, but the longer retention time then required will be uncomfortable for many living beings and will reduce the capacity of the measuring apparatus whereas the heat and water vapour given off will affect more strongly the result of the measurement and even slight leakages from the measuring chamber will have a stronger effect than in case of a short retention time.

The object of the invention is therefore to provide an improvement of said method and more in particular such an improvement that even at a short retention time an accurate measurement of the volume will nevertheless be possible by measuring a change in pressure caused by a change in volume.

According to the invention this object is preferably attained by a method characterized in that the measurement is performed in a chamber like indicated in which apart from the body to be measured at least a major part is filled with a solid filler material having a plurality of interconnected cavities.

It has been found that the compression will occur thereby almost purely isothermally so that a short retention time of e.g. 10 seconds will suffice. Apparently the solid filler material absorbs the heat generated by the compression sufficiently within a normal measuring range due to the very large total surface in the cavities thereof while the filler material shields the body to be measured from the major part of the contents of the chamber such that the emission of heat and water vapour by said body do not affect the measurement unfavourably to a noticeable extent.

For achieving a still higher accuracy the measurement may be performed in a way known in principle by measuring the pressure differential upon simultaneously quickly changing the volume of both the measuring chamber and of a reference chamber to a proportionate extent. The invention now also relates to such a system that in accordance with a preferred embodiment of the invention may be improved further by filling the volume of the reference chamber for at least a major part thereof with such a material having a plurality of interconnected cavities. On the basis of the pressure differential between the chambers the volume of the body in the measuring chamber may then be determined while the compression within the reference chamber will occur also isothermally because the reference chamber has also been filled with a filler material.

A measuring chamber for performing the above indicated method comprising means for taking up bodies to be measured in said chamber, means for closing said chamber, means for measuring the pressure within said chamber and means for changing the volume of said chamber in a quick and controlled manner to a known extent is in accordance with the invention characterized in that said chamber is filled at least for a major part thereof with a solid material having a plurality of interconnected cavities; the same applying to an optionally used reference chamber.

Furthermore it is preferred that within the measuring chamber the solid filler material is embodied such that said filler material is agglomerated into one or more solid filling bodies in which a recess is provided for said solid body the volume of which is to be measured, said recess being in a shape adapted broadly to the shape of said body.

Preferably the filler material is elastic. Consequently the recess for the body to be measured may be made such that in case of all bodies to be measured or a large number thereof these bodies will be enclosed by said filler material while exerting some pressure on the bodies. Nevertheless some room may be left in the filler material e.g. at the side of the face of human beings and animals.

The invention will now be elucidated further in detail with reference to the annexed drawing diagrammatically showing a measuring apparatus according to the invention.

Within a measuring chamber 1 there has been provided a filling consisting of elastic foamed polyurethane having a sponge structure, that is having intercommunicating pores. Said filling has been mounted in the form of a number of blocks 2 leaving a free space 3 in which the body to be measured may be inserted. The chamber possesses an access door that may be closed hermetically. Between said door and the body to be measured there may be provided some easily removable blocks of the filler material. The wall of the chamber may be transparent or may be provided with one or more windows. For the measurement of the volume of human beings there has been diagrammatically shown a free space 3 for the upright position, which position may however also be a seated position or recumbent position. The interior cavities of the body taking part in the compression are diagrammatically represented by a lung cavity 4. At the sides coinciding with the free space 3 the blocks 2 will of course usually not possess flat boundary surfaces like indicated in the drawing when human beings or animals have to be measured unless the filler material chosen possesses so high an elasticity that even in such a case an almost complete enclosure of the body to be measured is achieved without causing an objectionable indentation pressure.

A reference chamber 5 has been filled with the same filler material in the form of blocks 6.

Each one of the chambers 1 and 5 communicates with a cylinder including a piston for the compression of the contents thereof. At 13 the chamber 1 is in open communication with a cylinder 7 in which there has been inserted a piston 8 mounted on a pistonrod 9, whereas at 14 the chamber 5 is in open communication with a cylinder 10 including a piston 11 mounted on the same pistonrod 9, said pistonrod running through a packing gland 12. At 15 the cylinder 7 is open whereas the cylinder 10 possesses an opening at 16.

Between the chambers 1 and 5 there has been indicated diagrammatically a pressure differential gauge at 17.

In order to keep the air in the chambers 1 and 5, respectively, everywhere constantly under the same uniformly equilibrated pressure upon compression by means of the pistons 8 and 11 and if such may be desired in view of the blocks 2 and 6, the blocks may be provided with the channels 18 connected in such a manner that they constitute a direct connection to the openings at 13 and 14. Usually this will however not be necessary because of the porosity of said blocks as well as optionally because of the rapid pressure equilibration through narrow gaps at the boundary surfaces of said blocks.

Upon insertion of a body to be measured within the free space 3 of the chamber 1 the pistonrod 9 is moved to the left over a fixed down distance whereby the piston 8 decreases the volume of that part of the cylinder 7, communicating with the chamber 1 and increases the pressure within the chamber 1. Simultaneously the piston 11 increases the pressure within the reference chamber 5. The diameters of the pistons 8 and 11 have been chosen such that upon a same stroke of the pistonrod 9 the pistons 8 and 11 will displace a volume directly proportional with the free volume of the chambers 1 and 5, respectively, that is to say the volume thereof minus the volume of the filler material.

The said volume of the filler material may easily be determined by operating the pistonrod 9 for increasing the pressure within the chambers 1 and 5 without the body to be measured being present in the free space 3. By measuring the absolute pressure in each one of the chambers 1 and 5, for example by alternately disconnecting the pressure gauge from chamber 1 when performing the measurement in the chamber 5 and from chamber 5 when performing the measurement in chamber 1 it is possible to determine the effective free volume of each one of said chambers.

It may easily be deduced that upon isothermal compression the volume of the body to be measured is determined by the e.g. thus found free initial volume of the chamber 1 including the volume of the joint 13 and the cylinder space 7 to the left of the piston 8, the initial pressure in the two chambers 1 and 5, the change in volume in the cylinder 7 caused by the piston 8 and the pressure differential measured at 17 upon compression.

When measuring the volume of human beings the free volume of chamber 11 is e.g. about 600 liters, of chamber 5 e.g. about 52 liters and the change in volume of the cylinder 7 e.g. about 2.9 liters. The rate in which the pistonrod 9 is moved corresponds e.g. to a pressure increase rate of 50 mm head of water per second but may be chosen to be higher without any objection e.g. corresponding to a pressure increase rate of 200 mm head of water per second. The human body can normally stand much quicker pressure increases very well.

Preferably the pressure gauge 17 is in the form of a self-recording pressure meter.

The fillermaterial does not have to meet stringent requirements with respect to chemical and physical properties thereof. The polyurethane foam having a sponge structure used in performing the tests had a density of 15 kg/m$^3$ and was supplied by Recticel, Kesteren, The Netherlands. The linear cross section of the pores amounted to about 1 mm. The elasticity was so high that the material could easily be compressed elastically to at least 50% of the initial volume while elasticities up to 80–90% elastic compressibility may easily be achieved although such elasticities are usually not required. A honeycomb construction of aluminium strip material may e.g. also be used, the chambers therein all communicating with each other and having linear dimensions of probably preferably at most 8 mm, preferably 5–6 mm. The filler material may e.g. also be wool or cotton or consist of metal strip material and the like having a large total surface.

I claim:

1. Method for measuring the volume of solid bodies by plethysmometry, i.e. by measuring the change in pressure caused by changing the volume to a predetermined known extent of a chamber in which the bodies to be measured are taken up, and which is closed from the surroundings, characterized in that, apart from the body to be measured the space within the chamber is filled for at least a major part thereof with a solid filler material having a plurality of interconnected cavities.

2. Method according to claim 1, in which the measurement is performed by measuring the pressure differential upon simultaneously quickly changing the volume of both the measuring chamber and of a reference chamber proportionally, characterized in that, the volume of the reference chamber is filled for at least a major part thereof with a filler material having a plurality of interconnected cavities.

3. Measuring apparatus for measuring the volume of a solid body by measuring the change in pressure resulting from changing the volume of a chamber containing the body by a predetermined amount, said apparatus comprising:

a measuring chamber for receiving a body to be measured, the chamber having an opening for positioning the body in the chamber, the opening being closable so that the interior of the chamber is isolated from the ambient environment;

a solid material having a plurality of interconnected cavities disposed in the interior of the chamber and filling a large part thereof;

means for changing the volume of a space including the interior of said chamber by a predetermined amount; and means for measuring the change in pressure resulting from the change in volume, the change in pressure being representative of the volume of the body being measured.

4. Measuring apparatus according to claim 6, wherein a recess is provided in the solid material for receiving the body to be measured, said recess having a shape roughly corresponding to the shape of the body being measured.

5. Measuring apparatus according to claim 3 or 4, wherein the solid material is agglomerated into a plurality of blocks.

6. Measuring apparatus according to claim 3 or 4, wherein said filler material is elastic.

7. Measuring apparatus according to claim 5, wherein interconnected channels are formed in said blocks for rapidly equilibrating pressure in said chamber.

8. Measuring apparatus according to claim 3 or 4, further comprising a reference chamber, and wherein said means for changing the volume is positioned so as to simultaneously change the volume of the space including the interior of the measuring chamber and to change by a proportional amount the volume of a second space including the interior of the reference chamber, said means for measuring the change in pressure measuring the pressure differential between said measuring chamber and said reference chamber resulting from the changes of volume.

9. Measuring apparatus according to claim 8, further comprising solid filler material having interconnected compartments located in the interior of said reference chamber.

* * * * *